United States Patent
Mezei et al.

(10) Patent No.: US 7,851,627 B2
(45) Date of Patent: Dec. 14, 2010

(54) OPTICALLY ACTIVE CARBAMATES, PROCESS FOR PREPARATION THEREOF AND USE THEREOF AS PHARMACEUTICAL INTERMEDIATES

(75) Inventors: Tibor Mezei, Budapest (HU); EniköMolnar, Erd (HU); Péter Trinka, Budapest (HU); Ferenc Bartha, Tiszavasvári (HU); Zoltán Katona, Egor (HU); Györgyi Vereczekeyné Donath, Budapest (HU); Kálmán Nagy, Budapest (HU); Lászlö Pongo, Kerepes (HU); Gyula Lukacs, Budapest (HU); Márta Porcs-Makkay, Pomáz (HU); Zsuzsanna Évinger, Budapest (HU); Gyula Simig, Budapest (HU)

(73) Assignee: Egis Gyogyszergyar Nyilvanosan Mukodo Reszvenytarsasag, Budapest (HU)

( * ) Notice: Subject to any disclaimer, the term of this patent is extended or adjusted under 35 U.S.C. 154(b) by 243 days.

(21) Appl. No.: 12/096,636

(22) PCT Filed: Dec. 8, 2006

(86) PCT No.: PCT/HU2006/000109

§ 371 (c)(1),
(2), (4) Date: Nov. 10, 2008

(87) PCT Pub. No.: WO2007/066163

PCT Pub. Date: Jun. 14, 2007

(65) Prior Publication Data

US 2009/0221823 A1    Sep. 3, 2009

(30) Foreign Application Priority Data

Dec. 8, 2005    (HU) .................................... 0501139

(51) Int. Cl.
*C07D 241/04*    (2006.01)
*C07D 295/00*    (2006.01)

(52) U.S. Cl. ..................................... 544/389; 544/396

(58) Field of Classification Search ................ 544/389, 544/396

See application file for complete search history.

(56) References Cited

U.S. PATENT DOCUMENTS

| | | | | |
|---|---|---|---|---|
| 2,709,169 | A | * | 5/1955 | Morren ........................ 544/396 |
| 5,478,941 | A | | 12/1995 | Cossement ................... 544/383 |
| 6,803,465 | B2 | | 10/2004 | Kudo ........................... 544/389 |

FOREIGN PATENT DOCUMENTS

| | | |
|---|---|---|
| BE | 508650 | 2/1952 |
| BE | 501277 | 8/1952 |
| GB | 2076403 | 12/1981 |

* cited by examiner

*Primary Examiner*—James O Wilson
*Assistant Examiner*—Erich A Leeser
(74) *Attorney, Agent, or Firm*—Jonathan Myers

(57) ABSTRACT

The present invention is related to 1-[(4-chlorophenyl)-phenylmethyl]-4-(2,2,2-trichloroethoxycarbonyl)-piperazine of the Formula (IV) and optically isomers thereof, process for preparation thereof and the use of the compound of the Formula (IV) in the preparation of 1-(4-chlorophenyl)-phenylmethyl-piperazine and optical isomers and salts thereof. 1-(4-chlorophenyl)-phenylmethyl-piperazine and optical isomers thereof are important intermediates in the preparation of non-sedating antihistamine-type active pharmaceutical ingredients.

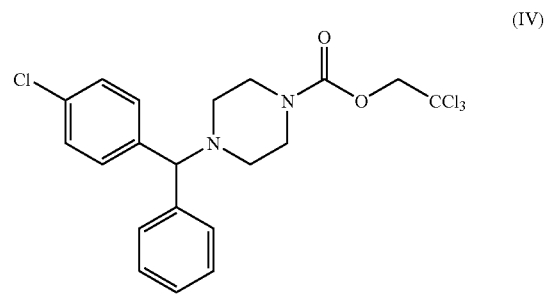

(IV)

33 Claims, No Drawings

OPTICALLY ACTIVE CARBAMATES, PROCESS FOR PREPARATION THEREOF AND USE THEREOF AS PHARMACEUTICAL INTERMEDIATES

CROSS REFERENCE TO RELATED APPLICATIONS

This application is the U.S. national phase of PCT application PCT/HU2006/000109, filed Dec. 8, 2006, published 14 Jun. 2007 as WO 2007/066163, and claiming the priority of Hungarian patent application P0501139 itself filed 8 Dec. 2005, whose entire disclosures are herewith incorporated by reference.

TECHNICAL FIELD OF THE INVENTION

The present invention is related to 1-[(4-chlorophenyl)-phenylmethyl]-4-(2,2,2-trichlorocarbethoxy)-piperazine of the Formula (IV)

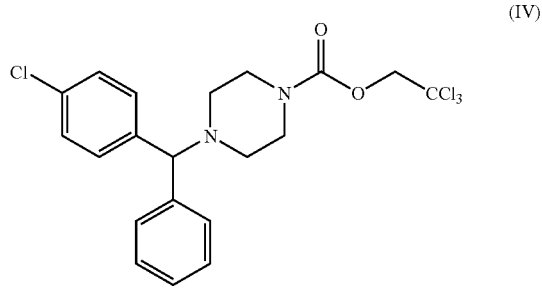

and its optical isomers, process for preparation thereof and the use of 1-[(4-chlorophenyl)-phenylmethyl]-4-(2,2,2-trichlorocarbethoxy)-piperazine of the Formula (IV) in the preparation of 1-(4-chlorophenyl)-phenylmethyl-piperazine of the Formula (I)

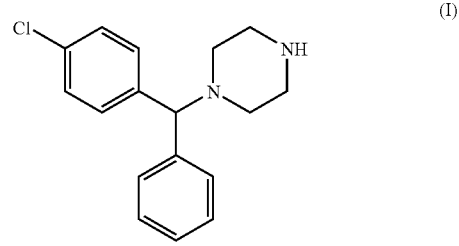

and its optical isomers and salts. 1-(4-chlorophenyl)-phenylmethyl-piperazine of the Formula (I) and its optical isomers are important pharmaceutical intermediates in the preparation of non-sedating antihistamine type active pharmaceutical ingredients.

TECHNICAL BACKGROUND OF THE INVENTION 1-(4-chlorophenyl)-phenylmethyl-piperazine of the Formula (I) is an important intermediate in the preparation of the active pharmaceutical ingredient known under the International Nonproprietary Name cetirizine. Cetirizine, which is chemically {2-[4-{(4-chlorophenyl)-phenylmethyl}-1-piperazinyl]-ethoxy}-acetic acid, is a non-sedating type antihistamine active ingredient suitable for the treatment of allergy. The effect of cetirizine is based on its selective interaction with histamine $H_1$ receptors inhibiting the histamine release.

Cetirizine is a racemic compound which is per se useful in the therapy. It is known from the state of the art that the administration of the levorotatory enantiomer, (−)-cetirizine is pharmacologically advantageous since during the administration of (−)-cetirizine, less side effects are experienced. (−)-cetirizine is an individual active pharmaceutical ingredient known by the International Nonproprietary Name levocetirizine.

There are several approaches known in the state of the art for the synthesis of optically active compounds.

According to one of these approaches, the racemic end product is prepared and the optically pure enantiomer is obtained in the final step by resolving the racemate.

According to the second approach, the optically active intermediate is prepared in the early phase of the synthesis process and subsequently such a synthetic route is developed, which ensures that the configuration of the desired optical center is retained and prevents the racemization thereof.

For economical reasons, it is desirable to carry out the separation of the optical isomers in an early stage of the synthesis process.

The value of the materials used in the early phase of the synthesis is generally lower than that of the intermediates used in the later stages. This approach usually results in environmental benefits as well, since the side products of the early steps of the synthesis can be more easily disposed of or recycled than those obtained in later stages.

According to a generally accepted procedure in the field of the synthesis of optically active chemicals, those synthesis routes are preferred which allow the use of a previously resolved intermediate known from the art or alternatively, the separation process of the optical isomers provides good yield or the intended optically active intermediate is commercially available.

According to the state of the art, there are three known processes for the preparation of optically active forms of 1-(4-chlorophenyl)-phenylmethyl-piperazine of the Formula (I).

According to the process disclosed in GB Patent No. 2 225 321, racemic 1-(4-chlorophenyl)-phenylmethyl-piperazine is resolved using 2 molar equivalent amount of (R)-tartaric acid and the tartarate salt having unsatisfactory optical purity obtained after three recrystallizations was neutralized. The thus obtained base was crystallized three times from hexane. The process provided (R)-(−)-1-(4-chlorophenyl)-phenylmethyl-piperazine in the yield of 6.3%. This method is not suitable for the use in the pharmaceutical industry since neither the product purity nor the yield are satisfactory.

Similarly to the above-described process, the general method for the separation of the optical isomers comprises preparing diastereomeric salts using an optically active acid, which is the so-called resolving acid. Physical properties of the thus obtained diastereomeric salts (i.e. melting point, solubility etc.) formed from the two optical isomers of the basic compound differ from each other.

Generally, the difference in physical properties of the two optical isomers of the optically active base are significant if the optical center of the optically active base is sterically closely located to the basic nitrogen atom which participates in salt formation.

The separation of the optical isomers of 1-(4-chlorophenyl)-phenylmethyl-piperazine of the Formula (I) is a difficult problem because 1-(4-chlorophenyl)-phenylmethyl-piperazine of the Formula (I) contains two basic nitrogen atoms. Although one of said nitrogen atoms is sterically closely located to the optical center, this nitrogen atom is sterically hindered therefore the salt formation with this nitrogen atom is hampered. The nitrogen atom distant from the optical center in position 4 undergoes salt formation much more easier.

Furthermore, the resolution of such compounds is complicated by the fact that due to the presence of two basic nitrogen atoms, two molar equivalents of the resolving acid shall be used for salt formation.

Since the optical isomers of racemic 1-(4-chlorophenyl)-phenylmethyl-piperazine of the Formula (I) can not be separated with good yield due to the two basic nitrogen atoms, another processes were developed.

In European Patent Application No. 1 236 722, racemic 1-(4-chlorophenyl)-phenylmethyl-piperazine of the Formula (I) was acylated in the position 4 and the tertiary butoxycarbonylated derivative of the Formula (V)

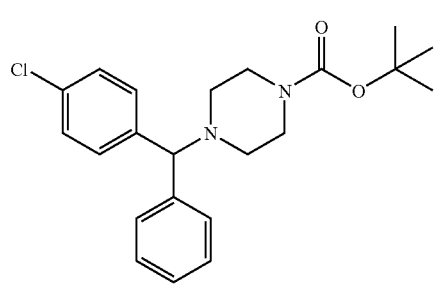

(V)

was resolved. The acylation in position 4 resulted in that there is one basic nitrogen atom present in the molecule, therefore the amount of the resolving acid can be decreased to one molar equivalents. Salt formation subsequent to acylation takes place at the position sterically close to the optical center, thus the efficacy of the separation could be increased.

The butoxycarbonyl derivative of the Formula (V) was resolved using D-(+)-O,O-dibenzoyl-tartaric acid as resolving acid and the primary product was obtained with an enantiomeric purity of 78%. Subsequently the protecting group was removed by hydrolysis and the base was recrystallized several times.

The disadvantage of the above-mentioned process resides in the fact that the introduction and hydrolytic removal of the protecting group is costly and the yield is only about 30% calculated on the basis of the amount of racemic 1-(4-chlorophenyl)-phenylmethyl-piperazine of the Formula (I).

It is known according to the state of the art that only those protecting groups can be used at the nitrogen atom in position 4 of the piperazine ring of 1-(4-chlorophenyl)-phenylmethyl-piperazine of the Formula (I), which can be removed under mild conditions at low temperature in non-aqeuous solution without the racemization of the optical center.

According to our experience, optically active 1-(4-chlorophenyl)-phenylmethyl-piperazine of the Formula (I) is transformed slowly into the corresponding racemic compound in acidic or basic solution even at room temperature. Racemization proceeds rapidly in aqueous alkaline solution, therefore those protecting groups, which are removed by alkaline hydrolysis i.e. acetyl or ethoxycarbonyl group, can not be used without significant racemization.

According to the process disclosed in European Patent No. 617 028, the optical center is prepared in the early phase of the synthesis. (R)-(−)-1-(4-chlorophenyl)-phenylmethylamine of the Formula (VI)

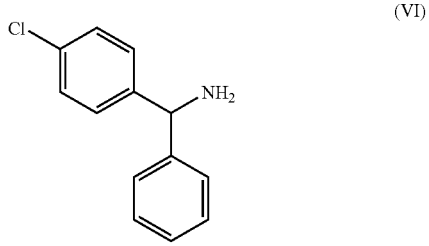

(VI)

is used as the starting substance. Said compound of the Formula (VI) can be prepared according to the method of Ingold and Wilson using camphorsulphonic acid (J. Chem. Soc. 1933, 1493) or using the process according to Clemo and Gadner in an aqueous solution with (+)-tartaric acid (J. Chem. Soc. 1939, 1958).

The synthesis of the piperazine ring of 1-(4-chlorophenyl)-phenylmethyl-piperazine of the Formula (I) is carried out by cyclization reaction. For this reaction, N-substituted derivatives of N,N-bis-(2-chloroethyl)-amine, such as N,N-bis-(2-chloroethyl)-4-methyl-benzenesulphonamide of the Formula (VII)

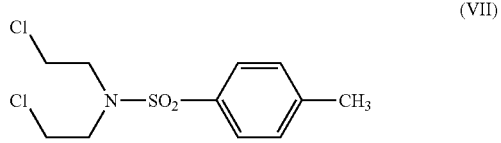

(VII)

or N,N-bis-(2-chloroethyl)-benzylamine of the Formula (VIII)

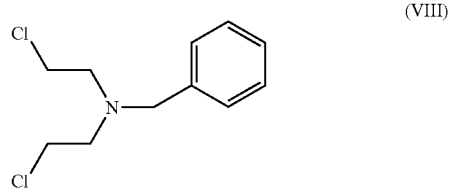

(VIII)

are used, since using N,N-bis-(2-chloroethyl)-amine is accompanied with side reactions and gum formation.

During the synthesis, optically active 1-[(4-chlorophenyl)-phenylmethyl]-4-[p-toluenesulphonyl]-piperazine of the Formula (II)

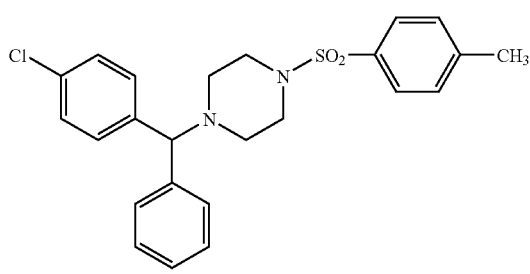

is obtained by reacting the optically active (4-chlorophenyl)-phenylmethylamine of the Formula (VI) and N,N-bis-(2-chloroethyl)-4-methyl-benzenesulphonamide of the Formula (VII), which is carried out by boiling the reactants in N,N-diisopropyl-ethylamine solvent at the temperature of 127° C. for four hours.

The product is crystallized and the p-toluenesulphonyl group is removed using 30% hydrogen bromide in acetic acid solvent by stirring for 24 hours. Under the harsh reaction conditions, four molar equivalents of 4-hydroxybenzoic acid are used to prevent the racemization. However, by the addition of 4-hydroxybenzoic acid, the process results in a contaminated product. The product is obtained in a yield of approximately 85%. The crude product is further purified by recrystallization.

According to different authors, (Oplatka, C. J. et al., Synthesis 1995, 766) using the above-mentioned process, the optically pure 1-(4-chlorophenyl)-phenylmethyl-piperazine of the Formula (I) can be obtained in a yield of 59%.

The disadvantage of the above-mentioned process resides in the fact that the hydrolysis of the toluenesulphonyl group requires harsh reaction conditions. Under such conditions, racemization occur which avoided by using further additives only. Using such additives constitute additional cost and said additives may contaminate the product.

In the field of organic chemistry, the benzyl group is often employed for the protection of nitrogen atoms. The benzyl group can be removed by catalytic hydrogenation using palladium-carbon catalyst at the temperature between 25 and 80° C. or using platinum or Raney-nickel catalyst at higher temperature and at higher hydrogen pressure.

By reacting N,N-(bis-chloroethyl)-benzylamine of the Formula (VIII) with 1-(4-chloromethyl)-methylphenylamine of the Formula (VI) in presence of an acid-binding agent, 1-[(4-chlorophenyl)-phenylmethyl]-4-benzyl-piperazine of the Formula (III)

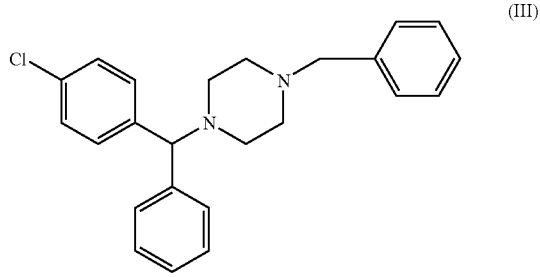

is obtained. However, the benzyl group cannot be removed selectively from 1-[(4-chlorophenyl)-phenylmethyl]-4-benzyl-piperazine of the Formula (III) by catalytic hydrogenation using palladium-carbon catalyst, since the N-(4-chlorobenzhydryl) moiety is eliminated faster, than the benzyl group.

According to the disclosure of U.S. Pat. No. 2,709,169, the removal of the N-benzyl group of racemic 1-[(4-chlorophenyl)-phenylmethyl]-4-benzyl-piperazine of the Formula (III) can be carried out with the yield of 75% by using the Raney-nickel catalyst. The reaction was carried out at the temperature of 150° C. and the pressure of 100 bar. However, when starting from the optically active benzyl-piperazine derivative, total racemization takes place at this high temperature, therefore the above-mentioned process is not suitable for the preparation of 1-[(4-chlorophenyl)-phenylmethyl]-piperazine of the Formula (I) in the optically active form.

In the case when the compound bis-(2-chloroethyl)-amine protected with the easily removable 2,2,2-trichloroethoxy-group in position 4 corresponding to the Formula (IX)

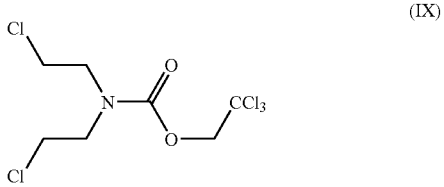

and 1-(4-chlorophenyl)-methylphenyl-amin of the Formula (VI) are reacted directly, the yield of the desired substituted piperazine derivative of the Formula (IV) is low, because under the conditions of cyclization at the temperature of 100° C. in presence of an acid-binding reagent, the 2,2,2-trichloroethoxy-carbonyl group is removed almost totally.

SUMMARY OF THE INVENTION

The objective of our research-development work was to develop a process for the preparation of the optically active forms of 1-(4-chlorophenyl)-methylphenyl-piperazine of the Formula (I) in good yield and in high optical and chemical purity in an economical process.

The above objective is solved by the process according to the present invention.

Very surprisingly, it has been found that 1-[(4-chlorophenyl)-phenylmethyl]-4-benzyl-piperazine of the Formula (III) can be reacted under mild conditions at room temperature with 2,2,2-trichloroethylchloroformate of the Formula (X)

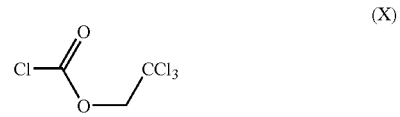

resulting in the formation of 1-[(4-chlorophenyl)-phenylmethyl]-4-(2,2,2-trichloroethoxycarbonyl)-piperazine of the Formula (IV) in a few hours.

Although there are a few examples in the art for the conversion of the N-benzyl group of the aliphatic amines into the corresponding carbamate by reacting said amines with chlorocarbonic acid esters, the chemical literature is silent about the transformation of the substituted piperazine derivatives into carbamates. The literature is also silent about the exchange of benzyl group for the alkoxycarbonyl group. It is very surprising that in this reaction, the cleavage of the 4-chlorobenzhydryl-group occurs in much less degree and the product of the side reaction is precipitated from the reaction mixture and it can be easily removed. Using optically active 1-(4-chlorophenyl)-methylphenyl-amine of the Formula (VI) as starting material, no racemization occur either during the preparation of 1-[(4-chlorophenyl)-phenylmethyl]-4-benzyl-piperazine of the Formula (III) or during the preparation of 1-[(4-chlorophenyl)-phenylmethyl]-4-(2,2,2-trichloroethoxy-carbonyl)-piperazine of the Formula (IV).

The product 1-[(4-chlorophenyl)-phenylmethyl]-4-(2,2,2-trichloroethoxycarbonyl)-piperazine of the Formula (IV) thus obtained can be transformed into 1-[(4-chlorophenyl)-phenylmethyl])-piperazine of the Formula (I) without the danger of racemization by removing the protecting 2,2,2-trichloroethoxycarbonyl group, which is carried out by treating the compound of the Formula (IV) with zinc and acetic acid in water-free environment in toluene solvent. After deprotection, 1-[(4-chlorophenyl)-phenylmethyl])-piperazine of the Formula (I) is isolated in the form of its fumarate salt of the Formula (XI).

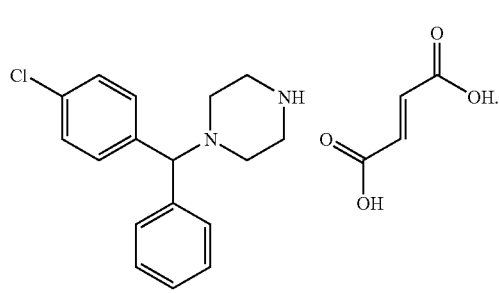

(XI)

1-[(4-chlorophenyl)-phenylmethyl]-piperazine of the Formula (XI) fumarate is new.

DETAILED DESCRIPTION OF THE INVENTION

According to the first aspect of the present invention, there is provided a process for the preparation of the racemic and the optically active forms of 1-(4-chlorophenyl)-phenylmethyl-piperazine of the Formula (I), which comprises reacting the racemic or the corresponding optically active form of 1-(4-chlorophenyl)-methylphenyl-amine of the Formula (VI) with N,N-(bis-2-chloroethyl)-benzylamine of the Formula (VIII) and converting the product racemic or optically active 1-(4-chlorophenyl)-phenylmethyl-4-benzyl-piperazine of the Formula (III) into 1-(4-chlorophenyl)-phenylmethyl-4-(2,2,2-trichloroethoxycarbonyl)-piperazine of the Formula (IV) by treating the compound of the Formula (III) with 2,2,2-trichloroethoxychloroformate, removing the protecting group and isolating the product 1-(4-chlorophenyl)-phenylmethyl-piperazine of the Formula (I) in the form of its fumarate salt. 1-(4-chlorophenyl)-phenylmethyl-piperazine fumarate (1:1) of the Formula (XI) is new.

In the present description, under the expression "acid addition salts" are meant the salts of the compound in question formed with organic or inorganic acids. Acids suitable for salt formation include inorganic acids, such as hydrochloric acid, hydrogen bromide, phosphoric acid, nitric acid and sulphuric acid; and organic acids, e.g. formic acid, acetic acid, propionic acid, maleic acid, fumaric acid, succinic acid, lactic acid, malic acid, tartaric acid, citric acid, ascorbic acid, malonic acid, oxalic acid, mandelic acid, picric acid, glycolic acid, phtalic acid, benzenesulphonic acid, p-toluenesulphonic acid, naphtalenesulphonic acid or methanesulphonic acid. Carbonates, hydrogen-carbonates, sulphides, hydrogen-sulphites and sulphites are also considered an acid addition salt formed with an inorganic acid.

According to a further aspect of the present invention, there are provided the optically active forms of 1-[(4-chlorophenyl)-phenylmethyl]-4-benzyl-piperazine of the Formula (III) and the acid addition salts thereof.

According to a further aspect of the present invention, there is provided a process for the preparation of the optically active forms of 1-[(4-chlorophenyl)-phenylmethyl]-4-benzyl-piperazine of the Formula (III) and the acid addition salts thereof. Enantiomers of the compound of the Formula (III) are prepared by reacting an optically active form of (4-chlorophenyl)-phenylmethyl-amine of the Formula (VI) with N,N-bis-(2-chloroethyl)-benzylamine of the Formula (VIII).

The (4-chlorophenyl)-phenylmethylamine of the Formula (VI) can be used as free base or as hydrochloride. The N,N-bis-(2-chloroethyl)-benzylamine of the Formula (VIII) is used in 1.0 to 1.5-fold, preferably 1.1-fold molar amount calculated on the basis of the amount of the compound of the Formula (VI).

The acid-binding agents suitable for use in the reaction include inorganic bases, e.g. alkali metal or alkali earth metal carbonates or hydrocarbonates or organic bases, e.g. pyridine or tributylamine. The acid-binding agent is used in the reaction in 3.0 to 5.0-fold molar amount calculated on the basis of the amount of N,N-bis-(2-chloroethyl)-benzylamine of the Formula (VIII). In the case when (4-chlorophenyl)-phenylmethylamine of the Formula (VI) is used in the form of a salt, the amount of the acid-binding agent is increased with the amount necessary for the neutralization.

The reaction is preferably carried out in a high-boiling indifferent solvent, e.g. in methyl or ethyl cellosolve, ethylene glycol, 1-butanol, isobutanol, cyclohexanol; or in a bipolar aprotic solvent, e.g. N,N-dimethyl-formamide, dimethyl-sulphoxide. The reaction can also be carried out in a high-boiling ether type solvent, e.g. diisobutylether, dioxane or in an aromatic solvent, e.g. toluene.

The reaction rate can be increased by using catalysts. The suitable type of catalysts include alkali metal halogenides and phase-transfer catalysts. As an alkali metal halogenide, sodium or potassium iodide or bromide, as a phase transfer catalyst, quaternary butylammonium halogenides can be used.

The reaction is carried out at a temperature between 80 and 140° C., preferably at a temperature between 100 to 110° C. The reaction time, depending on the reaction temperature is approximately 1 to 8 hours, preferably 2 to 4 hours.

According to a further aspect of the present invention, there is provided 1-[(4-chlorophenyl)-phenylmethyl]]-4-[(2,2,2-trichloroethyl)-oxy-carbonyl]-piperazine of the Formula (IV), its racemic and optically active forms and acid addition salts thereof.

A further aspect of the present invention is related to a process for the preparation of 1-[(4-chlorophenyl)-phenylmethyl]]-4-[(2,2,2-trichloroethyl)-oxycarbonyl]-piperazine of the Formula (IV), which comprises reacting 1-[(4-chlorophenyl)-phenylmethyl]-4-benzyl-piperazine of the Formula (III) with 2,2,2-trichloroethylchloroformate of the Formula (V).

The reaction can be carried out by starting from racemic or optically active form essentially containing the single enantiomer of 1-[(4-chlorophenyl)-phenylmethyl]-4-benzyl-piperazine of the Formula (III), wherein either the racemic or the optically active product is obtained.

In the reaction, the free base of 1-[(4-chlorophenyl)-phenylmethyl]-4-benzyl-piperazine of the Formula (III) is reacted preferably with 1.0 to 1.2 molar equivalent amount of 2,2,2-trichloroethylchloroformate of the Formula (V). Preferably, 1.05 mole of the compound of the Formula (V) is used for each mole of the compound of the Formula (III).

It is not necessary to use an acid binding agent during the reaction, since the product of the Formula (IV) forms salt with the hydrochloric acid formed in the reaction; however, if desired, an acid binding agent can be used. Compounds useful as acid-binding agents can be selected from inorganic bases, e.g. sodium carbonate, potassium carbonate or from organic bases, e.g. pyridine, tributylamine of triethylamine.

The reaction is carried out in an indifferent solvent, preferably of an aromatic type, e.g. toluene, benzene. Dipolar aprotic or ether-type solvents can also be used, e.g. N,N-dimethyl-formamide, dimethyl-sulphoxide, diisobutylether, diethylether, tetrahydrofurane or dioxane.

In the reaction of 1-[(4-chlorophenyl)-phenylmethyl]-4-benzyl-piperazine of the Formula (III) and 2,2,2-trichloroethylchloroformate of the Formula (V), the side product 1-benzyl-4-(2,2,2-trichloroethoxycarbonyl)-piperazine of the Formula (XII)

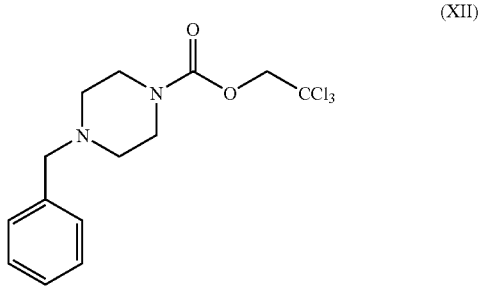

is formed in the acylation reaction of the 1-(4-chlorobenzhydryl)-group of the compound of the Formula (IV) in an amount of 5 to 25% by weight. The hydrochloride salt of the compound of the Formula (XII) crystallizes from aromatic solvent during the reaction and could be easily and fully removed.

The reaction is performed at a temperature between −20 and 40° C., preferably at a temperature between 15 and 20° C. The reaction time depending on the solvent and reaction temperature is usually 1 to 4 hours.

According to a further aspect of the present invention, there is provided a method for the preparation of 1-[(4-chlorophenyl)-phenylmethyl]-piperazine of the Formula (I) and fumarate salt thereof, which comprises removing the trichloroethoxycarbonyl protecting group from 1-[(4-chlorophenyl)-phenylmethyl]]-4-[(2,2,2-trichloroethyl)-oxycarbonyl]-piperazine of the Formula (IV) by reduction which comprises treating said compound with zinc and an acid.

The zinc is used in the reaction in 1 to 5 molar equivalent, preferably 1.5 to 2.5 molar equivalent amount calculated on the basis of the molar amount of the compound of the Formula (IV).

1-[(4-chlorophenyl)-phenylmethyl]]-4-[(2,2,2-trichloroethyl)-oxycarbonyl]-piperazine of the Formula (IV) can be used as free base or in the form of its hydrochloride salt. The use of the hydrochloride salt of the compound of the Formula (IV) is generally preferred.

The reaction is carried out in a solvent selected from water, aqueous hydrochloric acid or aqueous acetic acid solution or from organic solvents, i.e. ethers or aromatic solvents or the mixtures of the above.

The reaction temperature is between 0 and 50° C., preferably a temperature of 20 to 25° C. The reaction time is several hours.

During any of the above-mentioned processes, either racemic or the optically active forms of the starting substance can be used. Consequently either the corresponding racemic or the optically active intermediates are obtained as product.

According to a preferable embodiment of the process, the optically active 1-[(4-chlorophenyl)-phenylmethyl]-4-benzyl-piperazine of the Formula (III) is transformed in the optically active 1-[(4-chlorophenyl)-phenylmethyl]-piperazine of the Formula (a) or the fumarate salt thereof without the isolation of 1-[(4-chlorophenyl)-phenylmethyl]-4-(2,2,2-trichloroethyl)-piperazine of the Formula (IV) intermediate in a so-called "one-pot" process.

Further details of the invention are disclosed in the following examples without limiting the scope of the invention to said examples.

EXAMPLE 1

(R)-(+)-1-(4-chlorophenyl)-phenylmethyl-4-benzyl-piperazine dihydrochloride

Compound of the Formula (III)

To 200 ml of n-butanol are added 21.8 g (0.10 mol) of (R)-(−)-(4-chlorophenyl)-phenylmethylamine, 33.6 g (0.40 mol) of sodium hydrogencarbonate, 25.6 g (0.11 mol) of N,N-bis-(2-chloroethyl)-benzylamine hydrochloride and 1.0 g of sodium iodide with stirring. The mixture is stirred at the temperature of 110° C. for two hours, then cooled and stirred at the temperature of 0° C. for further two hours and the sodium chloride formed in the reaction was filtered.

The filtrate is evaporated in vacuo and the residue is dissolved in threefold volume of isopropanol. This solution is added dropwise to the mixture of 250 ml of isopropanol and 30 ml of concentrated aqueous hydrochloric acid solution. The crystalline product is filtered at 0° C., washed and dried.

Yield: 38.5 g (85.5%) off-white crystals.

Melting temperature, 245-246° C.

Elemental analysis {calculated on the basis of the Formula $C_{24}H_{25}ClN_2 \cdot 2HCl$ (449.9)}:

| Calculated: | C: 64.07 | H: 6.05 | Cl: 23.65 | N: 6.23 |
| Measured: | C: 63.85 | H: 6.12 | Cl: 23.44 | N: 6.28 |

Optical purity by chiral high performance liquid chromatography, 99.5%.

EXAMPLE 2

(R)-(−)-1-(4-chlorophenyl)-phenylmethyl-4-benzyl-piperazine

Compound of the Formula (III)

The procedure of Example 1 is followed with the difference that after filtering the inorganic salts off, the filtrate is concentrated in vacuo, the residue is dissolved in 250 ml of ethylacetate, the ethylacetate solution is washed with water, dried and the solvent is evaporated.

The yellow oily evaporation residue is dissolved in 150 ml of methanol at the product is crystallized at the temperature of −20° C. for 24 hours, the product base is filtered off, washed with methanol and dried.

Yield, 38.5 g (65.0%) off-white crystals.
Melting temperature, 76-78° C.
Elemental analysis {calculated on the basis of the Formula $C_{24}H_{25}ClN_2$ (376.9)}:

| Calculated: | C: 76.48 | H: 6.69 | Cl: 9.41 | N: 7.43 |
| --- | --- | --- | --- | --- |
| Measured: | C: 76.12 | H: 6.82 | Cl: 9.30 | N: 7.51 |

Optical purity (chiral high performance liquid chromatography): 99.9%

EXAMPLE 3

(S)-(−)-1-(4-chlorophenyl)-phenylmethyl-4-benzyl-piperazine dihydrochloride

The procedure described in Example 1 is followed with the difference that instead of R-(−)-(4-chlorophenyl)-phenylmethylamine, 21.8 g (0.1 mole) (S)-(+)-(4-chlorophenyl)-phenylmethylamine, instead of the solvent n-butanol, the same amount of methyl cellosolve (2-methoxyethanol) are used.

Yield: 33.1 g (73.7. %), off-white crystals
Melting point, 245-246° C.
Elemental Analysis {calculated on the basis of the Formula $C_{24}H_{25}ClN_2.2HCl$ (449.9)}:

| Calculated: | C: 64.07 | H: 6.05 | Cl: 23.65 | N: 6.23 |
| --- | --- | --- | --- | --- |
| Measured: | C: 64.04 | H: 6.16 | Cl: 23.74 | N: 6.12 |

Optical purity (chiral high performance liquid chromatography): 99.4%

EXAMPLE 4

(R)-(+)-1-(4-chlorophenyl)-phenylmethyl-4-benzyl-piperazine dihydrochloride

Compound of the Formula (III)

The procedure of Example 1 is carried out with the differences that instead of sodium hydrogencarbonate, 27.4 g (0.20 mol) of potassium carbonate and instead of n-butanol solvent, methyl cellosolve are used.

Yield: 38.5 g (85.5%) off-white crystals
Melting point, 245-246° C.
Elemental Analysis {calculated on the basis of the Formula $C_{24}H_{25}ClN_2.2HCl$ (449.9)}:

| Calculated: | C: 64.07 | H: 6.05 | Cl: 23.65 | N: 6.23 |
| --- | --- | --- | --- | --- |
| Measured: | C: 63.72 | H: 6.22 | Cl: 23.51 | N: 6.32 |

Optical purity (chiral high performance liquid chromatography): 99.4%

EXAMPLE 5

(R)-(+)-1-(4-chlorophenyl)-phenylmethyl-4-benzyl-piperazine dihydrochloride

Compound of the Formula (III)

The procedure of Example 1 is carried out with the difference that instead of sodium hydrogencarbonate, 40.4 g (0.40 mol) of triethylamine, instead of n-butanol, equal volume of dioxane solvent are used.

Yield: 35.4 g (75.6%) off-white crystals
Melting point, 245-246° C.
Elemental Analysis {calculated on the basis of the Formula $C_{24}H_{25}ClN_2.2HCl$ (449.9)}:

| Calculated: | C: 64.07 | H: 6.05 | Cl: 23.65 | N: 6.23 |
| --- | --- | --- | --- | --- |
| Measured: | C: 63.94 | H: 6.19 | Cl: 23.85 | N: 6.34 |

Optical purity (chiral high performance liquid chromatography): 98.9%

EXAMPLE 6

(R)-(+)-4-(4-chlorophenyl)-phenylmethyl-piperazine 1-carboxylic acid-2,2,2-trichloroethylester hydrochlorid (1:1)

Compound of the Formula (IV)

37.7 g (0.1 mol) of (R)-(−)-1-[(4-chlorophenyl)-phenylmethyl]-4-benzyl-piperazine free base are dissolved in 300 ml of toluene and to this solution, the solution of 23.3 g (0.11 mol) 2,2,2-trichloroethylchloroformate prepared in 50 ml of toluene is added dropwise. The turbid suspension is stirred at room temperature for two hours, the pH of the reaction mixture is adjusted to pH 1.0-1.5 with 10% by weight hydrochloric acid solution prepared in ethylacetate, the crystalline (1-benzyl-piperazine-4-(2,2,2-trichloroethyl)-carbamate by-product is filtered off, the filtrate is washed with aqueous sodium hydrocarbonate solution, the toluene layer is dried over sodium carbonate and after filtration, the filtrate is evaporated.

The yellow oily evaporation residue weighing approximately 53.5 g are dissolved in 160 ml of isopropylalcohol and at the temperature of 40-55° C., 37 ml of 15 g/100 ml isopropanolic hydrochloric acid solution (hydrochloric acid content 5.5 g, 0.15 mol) are added dropwise in 30 minutes under stirring. After the addition of the hydrochloric acid, the suspension is cooled to the temperature of −5° C. in one hour, the crystals are filtered after two hours stirring, filtered, washed with isopropanol and dried.

Yield, 37.1 g (74.5%) white crystals
Melting temperature, 244-246° C.
Elemental Analysis {calculated on the basis of the Formula $C_{20}H_{20}Cl_4N_2O_2.HCl$ (498.7)}

| Calculated: | C: 48.17 | H: 4.24 | Cl: 35.55 | N: 5.62 |
| --- | --- | --- | --- | --- |
| Measured: | C: 48.05 | H: 4.32 | Cl: 35.85 | N: 5.71 |

Optical purity (chiral high-performance liquid chromatography): 99.2%

EXAMPLE 7

(R)-(+)-4-(4-chlorophenyl)-phenylmethyl-piperazine-1-carboxylic acid 2,2,2-trichloroethylester Free Base of the Compound of the Formula (IV)

5.0 g (10 mmol) of the hydrochloride prepared according to the procedure of Example 6 are added to the mixture of 50 ml of water and 50 ml of ethylacetate and the pH of the mixture is adjusted to pH 14 by addition of 10% by weight sodium hydroxide solution under stirring. The two layers are separated, the ethylacetate layer is dried over potassium carbonate, filtered and the solvent is evaporated. The evaporation residue is dissolved in 20 ml of isopropanol and the product is crystallized.

Yield: 3.89 g (84.2%) white crystals
Melting temperature: 96-97° C.
Elemental Analysis {calculated on the basis of the Formula $C_{20}H_{20}Cl_4N_2O_2$ (462.2)}:

| Calculated: | C: 51.97 | H: 4.36 | Cl: 30.68 | N: 6.06 |
|---|---|---|---|---|
| Measured: | C: 51.84 | H: 4.52 | Cl: 30.85 | N: 5.97 |

Optical purity (chiral high performance liquid chromatography): 99.8%

EXAMPLE 8

(S)-(−)-4-(4-chlorophenyl)-phenylmethyl-piperazine 1-carboxylic acid-2,2,2-trichloroethylester hydrochloride (1:1)

Compound of the Formula (IV)

The procedure of the Example 6 is carried out with the difference that (S)-(−)-1-(4-chlorophenyl)-phenylmethyl-4-benzyl-piperazine dihydrochloride (compound of the Example 3) is used as starting material.

Yield: 33.1 g (66.4%) white crystals
Melting temperature, 242-246° C.
Elemental Analysis {calculated on the basis of the Formula $C_{20}H_{20}Cl_4N_2O_2 \cdot HCl$ (498.7)}

| Calculated: | C: 48.17 | H: 4.24 | Cl: 35.55 | N: 5.62 |
|---|---|---|---|---|
| Measured: | C: 48.22 | H: 4.38 | Cl: 35.14 | N: 5.79 |

Optical purity (chiral high performance liquid chromatography): 98.5%

EXAMPLE 9

(R)-(+)-4-(4-chlorophenyl)-phenylmethyl-piperazine 1-carboxylic acid 2,2,2-trichloroethylester The Free Base of the Compound of the Formula (IV)

The procedure according to Example 6 is carried out with the difference that the reaction is performed in N,N-dimethyl formamide solvent instead of toluene at the temperature of 15° C. and at the beginning of the reaction, 15.1 g (0.15 mol) triethylamine are added to the reaction mixture. After the reaction, the reaction mixture is poured into 300 ml of ice-water mixture, the product is extracted with ethylacetate, the organic layer is dried over sodium sulphate and the solvent is evaporated.

The thus obtained oily residue is dissolved in the 1:1 (v/v) hexane-diethylether solvent mixture, the product is crystallized, filtered, dried.

Yield, 28.9 g (62.6%) white crystals
Melting temperature, 96-97° C.
Elemental Analysis {calculated on the basis of the Formula $C_{20}H_{20}Cl_4N_2O_2$ (462.2)}:

| Calculated: | C: 51.97 | H: 4.36 | Cl: 30.68 | N: 6.06 |
|---|---|---|---|---|
| Measured: | C: 51.89 | H: 4.42 | Cl: 30.85 | N: 5.96 |

Optical purity (chiral high performance liquid chromatography): 99.0%

EXAMPLE 10

(R)-(−)-1-(4-chlorophenyl)-phenylmethyl-piperazine dihydrochloride

Compound of the Formula (I)

A vessel is charged with 250 ml of tetrahydrofurane, 25 ml of methanol and 5.0 ml (60 mmol) concentrated hydrochloric acid (37% by weight). The mixture is cooled to the temperature of 15° C. and under intense stirring, 5.5 g (84 mmol) pulverized zinc are added. Subsequently at a temperature between 5 to 10° C., 12.5 g (25.1 mmol) (R)-(+)-4-(4-chlorophenyl)-phenylmethyl-piperazine-1-carboxylic acid 2,2,2-trichloroethylester hydrochloride (compound of the Example 6) are added in several portions. The suspension is stirred for one hour at room temperature. At the end of the reaction, the unreacted zinc is filtered off, the filtrate is mixed with 150 ml of water and 150 ml of ethylacetate, the organic layer is separated, washed with aqueous 5% by weight sodium hydrogen carbonate solution, dried and the solvent is evaporated.

The residue is dissolved in 100 ml of ethylacetate and is added dropwise with stirring to 80 ml of 10 gi/00 ml hydrochloric acid solution prepared in ethylacetate. The suspension containing the crystalline salt, which starts precipitating almost instantly after the addition, is cooled, the product is filtered off, washed with diethylether and dried.

Yield: 7.7 g (85.4%) white crystals
Melting temperature, 198-202° C.
Elemental Analysis {calculated on the basis of the Formula $C_{17}H_{19}ClN_2 \cdot 2HCl$ (359.7)}:

| Calculated: | C: 56.76 | H: 5.88 | Cl: 29.57 | N: 7.79 |
|---|---|---|---|---|
| Measured: | C: 56.45 | H: 5.74 | Cl: 29.25 | N: 7.61 |

Optical purity (chiral high performance liquid chromatography): 98.7%

EXAMPLE 11

(R)-(−)-1-(4-chlorophenyl)-phenylmethyl-piperazine fumarate (1:1)

Compound of the Formula (XI)

13.0 g (0.2 mol) pulverized zinc are added to the mixture of 300 ml of toluene, 30 ml (0.52 mol) of glacial acetic acid (96% by weight) and 30 ml of methanol with stirring. Subsequently, in three equal portions during 15 minutes, 50.0 g (0.10 mol) (R)-(+)-4-(4-chlorophenyl)-phenylmethyl-piperazine-1-(2,2,2-trichloroethyl-carbamate) hydrochloride (compound of the Example 6) are added. The temperature of the greyish suspension is raising to approximately 41 to 45° C. in 10 minutes and intense evolution of carbon dioxide occurs.

After one hour, the suspension is filtered, the filtrate is mixed with 40 ml of water and 38.5 ml of 25% by weight ammonium hydroxide solution. The layers are separated, the toluene layer is dried over potassium carbonate and the solvent is evaporated.

The thus obtained yellow, oily evaporation residue (approx. 42 g) having the content of 75.5% calculated as free base, is dissolved in 500 ml of acetone and 12.8 g (0.11 mol) fumaric acid are added. The product, which initially separates in an oily form, is stirred for three hours at the temperature of 25° C. The crystalline product is filtered and dried until constant weight.

Yield, 31.3 g (77.8%) off-white crystals

Melting temperature, 146-148° C.

Elemental Analysis {calculated on the basis of the Formula $C_{21}H_{23}ClN_2O_4$ (402.9)}:

| Calculated: | C: 62.61 | H: 5.75 | Cl: 8.80 | N: 6.95 |
|---|---|---|---|---|
| Measured: | C: 62.27 | H: 5.72 | Cl: 8.79 | N: 6.84 |

Optical purity (chiral high performance liquid chromatography): 99.8%

EXAMPLE 12

(S)-(+)-1-(4-chlorophenyl)-phenylmethyl-piperazine fumarate (1:1)

Compound of the Formula (XI)

The procedure of the Example 11 is carried out with the difference that instead of using (R)-(+)-4-(4-chlorophenyl)-phenylmethyl-piperazine-1-(2,2,2-trichloroethyl)-carbamate hydrochloride salt, (S)-(−)-4-(4-chlorophenyl)-phenylmethyl-piperazine-1-(2,2,2-trichloroethyl)-carbamate hydrochloride salt (compound of Example 8) is used.

Yield: 24.2 g (60.0%) off-white crystals

Melting temperature, 145-148° C.

Optical purity (chiral high performance liquid chromatography): 99.2%

Melting temperature of the (S)-(+)-1-(4-chlorophenyl)-phenylmethyl piperazine base, 94-96° C. (hexane).

EXAMPLE 13

(R)-(−)-1-(4-chlorophenyl)-phenylmethyl-piperazine fumarate (1:1)

Compound of the Formula (XI)

45.0 g (0.10 mol) of (R)-(+)-1-[(4-chlorophenyl)-phenylmethyl]-4-benzyl-piperazine dihydrochloride are suspended in 300 ml of toluene, and during intense stirring, 50 g of ice, 50 ml of water and 25 ml of aqueous ammonium hydroxide solution are added. The layers are separated, the upper toluene layer is dried over potassium carbonate while stirring and filtered. To the filtrate, solution of 23.3 g (0.11 mol) 2,2,2-trichloroethylchloroformate prepared in 50 ml toluene are added dropwise. The turbid suspension is stirred for two hours at room temperature, the crystalline by-product is filtered off.

The filtrate is mixed with 30 ml of concentrated acetic acid (96% by weight), 30 ml of methanol and during intense stirring, 13.0 g (0.2 mol) of pulverized zinc are added. During the reaction, intense carbon dioxide evolution takes place. After one hour, the suspension is filtered, the filtrate is mixed with 40 ml of water and 38.5 ml 25% by weight ammonium hydroxide solution. The two layers are separated, the upper toluene layer is dried over potassium carbonate and the solvent is evaporated.

The residual yellow oil (approximately 35.2 g) is dissolved in 350 ml of acetone and while stirring, 11.6 g (0.1 mol) fumaric acid are added. The mixture is boiled until dissolution. The product is precipitated upon cooling. The suspension of the product is stirred for three hours at room temperature, the crystals are filtered, washed with diethylether and dried.

Yield, 27.9 g (65.8%) off-white crystals

Melting temperature, 146-148° C.

Optical purity (chiral high performance liquid chromatography): 99.6%

What is claimed is:

1. A process for the preparation of 1-[(4-chlorophenyl)-methylphenyl]-piperazine of the Formula (I)

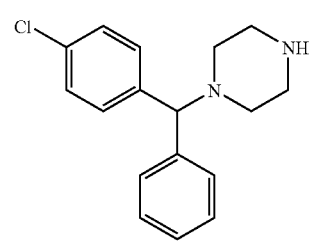

(I)

enantiomers and acid addition salts thereof, which comprises reacting the racemic or an optically active form of 1-[(4-chlorophenyl)-phenylmethyl]-4-benzyl-piperazine of the Formula (III)

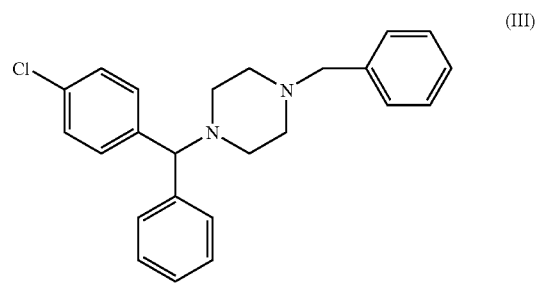

(III)

with 2,2,2-trichloroethylchloroformate of the Formula (X)

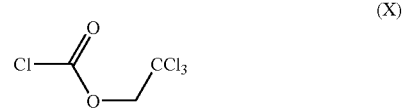

(X)

and converting the thus obtained 1-[(4-chlorophenyl)-phenylmethyl]-4-(2,2,2-trichloroethoxy-carbonyl)-piperazine of the Formula (IV)

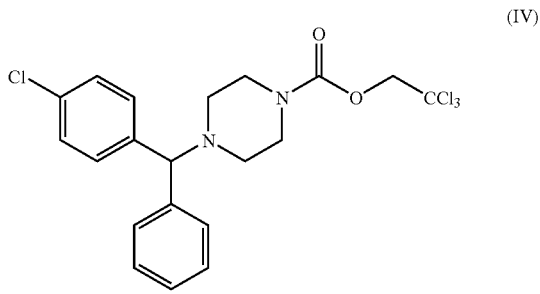

(IV)

into 1-[(4-chlorophenyl)-methylphenyl]-piperazine of the Formula (I).

2. A process for the preparation of 1-[(4-chlorophenyl)-methylphenyl]-piperazine of the Formula (I), or enantiomers and acid addition salts thereof, which comprises reacting racemic or an optically active form of 1-[(4-chlorophenyl)-phenylmethyl]-4-benzyl-piperazine of the Formula (III)

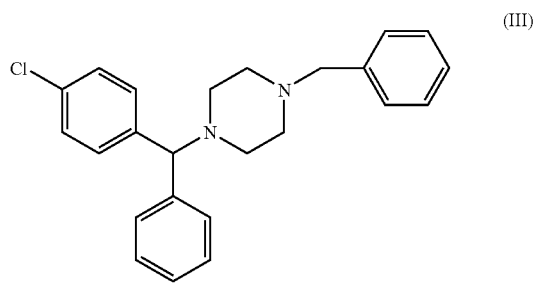

(III)

prepared by reacting 1-(4-chlorophenyl)-methylphenylamine of the Formula (VI)

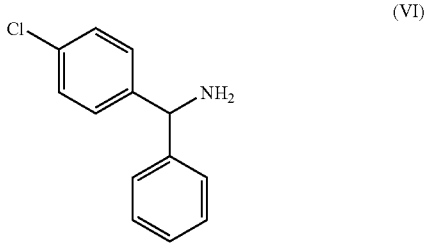

(VI)

and N,N-(bis-2-chloroethyl)-benzylamine of the Formula (VIII)

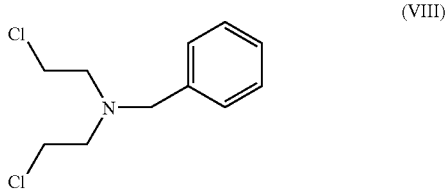

(VIII)

with 2,2,2-trichloroethylchloroformate of the Formula (X) and transforming the thus obtained 1-[(4-chlorophenyl)-phenylmethyl]-4-(2,2,2-trichloroethoxycarbonyl)-piperazine of the Formula (IV) into 1-[(4-chlorophenyl)-methylphenyl]-piperazine of the Formula (I).

3. A process for the preparation of 1-[(4-chlorophenyl>phenylmethyl]-4-(2,2,2-trichloroethoxycarbonyl)-piperazine of the Formula (IV), or enantiomers and acid addition salts thereof, which comprises reacting racemic or an optically active form of 1-[(4-chlorophenyl)-phenylmethyl]-4-benzyl-piperazine of the Formula (III) with 2,2,2-trichloroethylchloroformate of the Formula (X) and converting the thus obtained 1-[(4-chlorophenyl)-phenylmethyl]-4-(2,2,2-trichloroethoxycarbonyl) -piperazine of the Formula (IV) into its acid addition salt.

4. A process for the preparation of an optically active form of 1-[(4-chlorophenyl)-phenyl-methyl]-4-benzyl-piperazine of the Formula (III) and acid addition salts thereof, which comprises reacting (R)— or (S)-(4-chlorophenyl)-phenylmethylamine of the Formula (VI) with N,N-bis-(2-chloroethyl)-benzylamine of the Formula (VIII).

5. (R)—, and (S)-1-[(4-chlorophenyl)-phenyl-methyl]-4-benzyl-piperazine of the Formula (III) and acid addition salts thereof.

6. 1-[(4-chlorophenyl)-phenyl-methyl]-piperazine fumarate (1:1) of the Formula (XI)

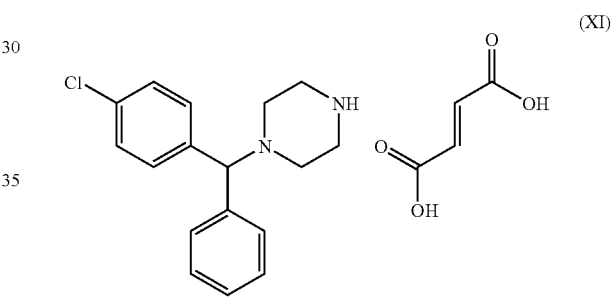

(XI)

and enantiomers thereof.

7. 1-[(4-chlorophenyl)-phenyl-methyl]-4-(2,2,2-trichloroethoxy-carbonyl)-piperazine of the Formula (IV)5 enantiomers and acid addition salts thereof.

8. 1-benzyl-4-(2,2,2-trichloroethoxy-carbonyl) -piperazine of the Formula (XII)

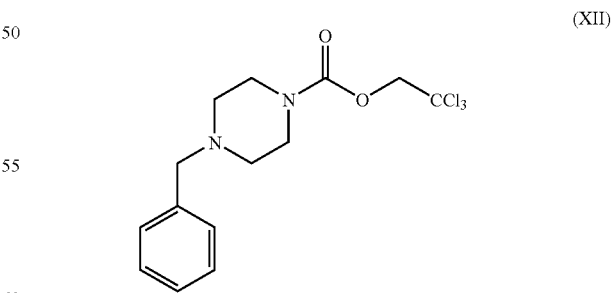

(XII)

and acid addition salts thereof.

9. The process according to claim 1 wherein 1-[(4-chlorophenyl)-phenylmethyl]-4-benzyl-piperazine of the Formula (III) is reacted with 1.0 to 1.2 molar equivalent, preferably 1.05 molar equivalent amount of 2,2,2-trichloroethylformate of the Formula (X).

10. The process according to claim 1 wherein the reaction of 1-[(4-chlorophenyl)-phenylmethyl]-4-benzyl-piperazine of the Formula (III) and 2,2,2-trichloroethylchloroformate of the Formula (X) is carried out in the presence of an inorganic or organic base constituting the acid binding reagent.

11. The process according to claim 10 wherein as inorganic base, an alkali metal or alkali earth metal hydrocarbonate or -carbonate, or as organic base, triethylamine, tributylamine or pyridine is used.

12. The process according to claim 1 wherein the reaction of 1-[(4-chlorophenyl)-phenylmethyl]-4-benzyl-piperazine of the Formula (III) and 2,2,2-trichloroethylchloroformate of the Formula (X) are carried out in a solvent selected from aromatic, polar aprotic or ether-type organic solvent.

13. The process according to claim 12 wherein as aromatic solvent, benzene or toluene, as polar aprotic solvent, N,N-dimethyl-formamide or dimethyl sulphoxide, as ether-type solvent, diisopropylether, diethylether, dioxane or tetrahydrofurane is used.

14. The process according to claim 1 wherein the reaction is carried out at the temperature between −20 and 40° C., preferably between 15 and 20° C.

15. The process according to claim 1 wherein the conversion of 1-[(4-chlorophenyl)-phenylmethyl]-4-(2,2,2-trichloroethoxy-carbonyl)-piperazine of the Formula (IV) into 1-[(4-chloro-phenyl)-methylphenyl]-piperazine of the Formula (I) is carried out by reduction.

16. The process according to claim 15 wherein the reduction is carried out by zinc in an acidic solution.

17. The process according to claim 16 wherein 1 to 5, preferably 1.5 to 2.5 molar equivalents amount of zinc are used calculated on the basis of the molar amount of 1-[(4-chlorophenyl)-phenyl-methyl]-4-(2,2,2-trichloroethoxy-carbonyl)-piperazine of the Formula (IV).

18. The process according to claim 1 wherein in the transformation of 1-[(4-chlorophenyl)-phenyl-methyl]-4-(2,2,2-trichloro-ethoxycarbonyl)-piperazine of the Formula (IV) into 1-[(4-chlorophenyl)-methylphenyl]-piperazine of the Formula (I), a solvent selected from water, aqueous acid solution, for example, aqueous acetic acid or hydrochloric acid solution, an aromatic solvent, for example toluene or mixtures thereof are used.

19. The processes according to claim 1 wherein the conversion of 1-[(4-chlorophenyl)-phenyl-methyl]-4-(2,2,2-trichloroethoxy-carbonyl)-piperazine of the Formula (IV) into 1-[(4-chlorophenyl)-methylphenyl]-piperazine of the Formula (I) is carried out at a temperature between 0 and 50° C., preferably between 20 and 25° C.

20. The process according to claim 1 wherein after the conversion of 1-[(4-chlorophenyl)-phenyl-methyl]-4-(2,2,2-trichloro-ethoxycarbonyl)-piperazine of the Formula (IV) into 1-[(4-chlorophenyl)-methylphenyl]-piperazine of the Formula (I), the product of the Formula (I) is obtained in the form of fumarate salt thereof.

21. The processes according to claim 2 wherein 1-(4-chloro-phenyl)-methylphenylamine of the Formula (VI) is used in 1.0 to 1.5 molar equivalent, preferably in 1.1 molar equivalent amount calculated on the basis of the molar amount of N,N-(bis-2-chloroethylethyl)-benzylamine of the Formula (VIII).

22. The process according to claim 2 wherein the reaction of 1-(4-chlorophenyl)-methylphenylamine of the Formula (VI) and N,N-(Ms-chloroethyl)-benzylamine of the Formula (VIII) is carried out in presence of an acid-binding reagent.

23. The process according to claim 22 wherein a basic inorganic salt, for example an alkali metal or alkali earth metal carbonate or hydrogencarbonate, preferably sodium hydrogencarbonate or an organic base, preferably triethylamine, tributylamine or pyridine is used as acid-binding reagent.

24. The processes according to claim 22 wherein the acid-binding reagent is used in 3 to 5 molar equivalent amount calculated on the basis of the molar amount of N,N-(bis-2-chloroethyl)-benzylamine of the Formula (VIII).

25. The processes according to claim 2 wherein the reaction of 1-(4-chlorophenyl)-methylphenylamine of the Formula (VI) and N,N-(bis-2-chloroethyl)-benzylamine of the Formula (VIII) is carried out in a polar protic, a polar aprotic, an aromatic-type or an ether-type solvent, for example, methyl cellosolve, ethyl cellosolve, ethyleneglycol, 1-butanol, isobutanol, cyclohexanol, N,N-dimethyl-formamide, dimethyl-sulphoxide, toluene, xylene, or diisobutylether.

26. The process according to claim 2 wherein the reaction of 1-(4-chlorophenyl)-methylphenylamine of the Formula (VI) and N,N-(bis-2-chloroethyl)-benzylamine of the Formula (VIII) is carried out in presence of a catalyst.

27. The process according to claim 26 wherein an alkali metal iodide or an alkali metal bromide, preferably potassium iodide is used as catalyst.

28. The process according to claim 26 wherein a phase-transfer catalyst, for example, a quaternary ammonium halogenide, for example, tetrabutylammonium bromide is used.

29. The process according to claim 2 wherein the reaction is carried out at a temperature between 80 and 140° C., preferably at a temperature between 100 and 110° C.

30. The processes according to claim 1 wherein (R)-(+)-1-[(4-chlorophenyl)-phenylmethyl]-4-benzyl-piperazine of the Formula (III) is used as starting material.

31. The process according to claim 2 wherein (R)-(−)-1-(4-chloro-phenyl)-methylphenylamine of the Formula (VI) is used as starting substance.

32. The process according to claim 4 wherein (R)-1-(4-chloro-phenyl)-phenylmethylamine of the Formula (III) is used as starting substance.

33. The process according to claim 15 wherein (R)-(+)-[(4-chloro-phenyl)-phenylmethyl]-4-(2,2,2-trichloroethoxycarbonyl)-piperazine of the Formula (IV) is used as starting material.

* * * * *